United States Patent [19]
Granger

[11] Patent Number: 5,533,521
[45] Date of Patent: Jul. 9, 1996

[54] INTERCHANGEABLE TISSUE MEASURING DEVICE

[75] Inventor: Richard N. Granger, Huntington, Conn.

[73] Assignee: United States Surgical Corporation, Norwalk, Conn.

[21] Appl. No.: 276,121

[22] Filed: Jul. 15, 1994

[51] Int. Cl.⁶ ................................................. A61B 5/103
[52] U.S. Cl. ............................................................. 128/774
[58] Field of Search .................................... 128/751, 754, 128/774; 227/175–178; 606/205–207

[56] References Cited

U.S. PATENT DOCUMENTS

| | | | |
|---|---|---|---|
| 4,312,363 | 1/1982 | Rothfuss et al. | 128/774 |
| 5,071,430 | 12/1991 | DeSalis et al. | 606/219 |
| 5,327,908 | 7/1994 | Gerry | 128/774 |
| 5,336,232 | 8/1994 | Green et al. | 606/151 |
| B1 5,040,715 | 4/1994 | Green et al. | 227/176 |

FOREIGN PATENT DOCUMENTS 216532  1/1987  European Pat. Off. .

Primary Examiner—Max Hindenburg

[57] ABSTRACT

A detachable tissue measuring cartridge is disclosed for use with a surgical actuating apparatus such as, for example a surgical stapling apparatus. In one embodiment of the tissue measuring cartridge a longitudinally movable actuating structure is utilized to drive a tissue measuring block, located in a housing of the cartridge, upwardly towards an opposing anvil member associated with the surgical apparatus to capture a tissue section therebetween. The thickness of the tissue captured between the anvil member and the tissue measuring block is measured by the amount of rise of the tissue measuring block out of the cartridge housing. Gradation lines may be provided on the sides of the block to give a visual indication of the tissue thickness. In an alternate embodiment, a tissue measuring block is initially disposed upwardly within a cartridge housing. As an anvil member is moved toward the tissue measuring block to capture a tissue section therebetween, the captured tissue forces the block down into the cartridge housing to again generate an indication of the tissue thickness. Various spring members may be provided to bias the tissue measuring blocks either upwardly or downwardly within the various cartridge housings. The embodiments of the tissue measuring cartridge may be provided alone or in combination with a surgical stapling or cutting apparatus in the form of a kit.

23 Claims, 7 Drawing Sheets

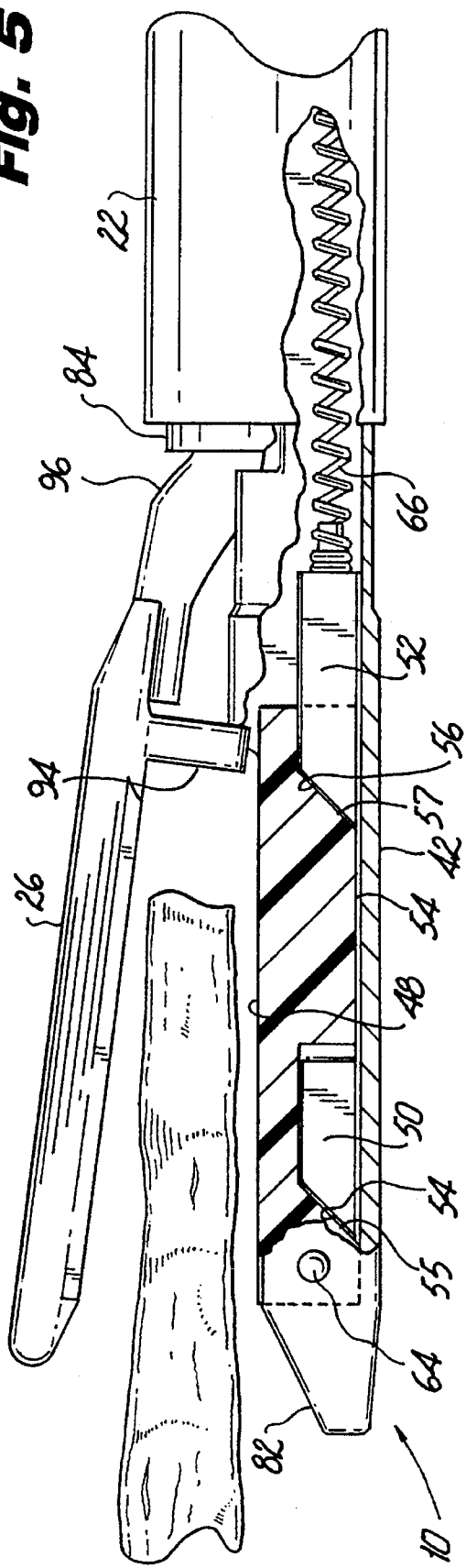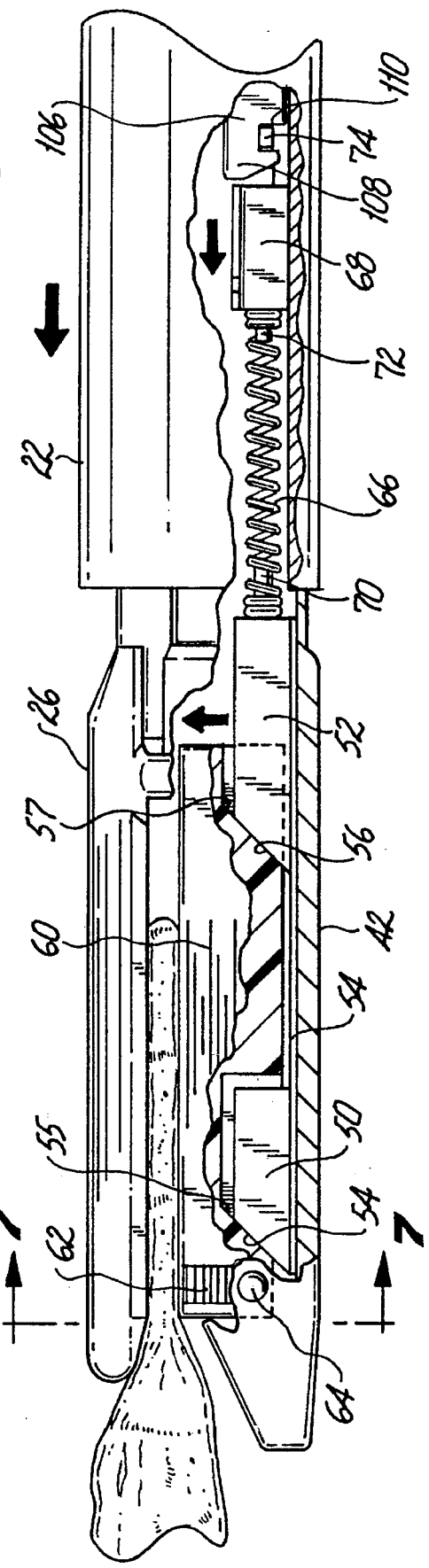

INTERCHANGEABLE TISSUE MEASURING DEVICE

BACKGROUND

1. Technical Field

The technical field relates to a tissue thickness measuring device and, more particularly, to an interchangeable tissue measuring cartridge suitable for use with a surgical stapler apparatus to measure tissue thickness.

2. Discussion of Related Art

During various surgical procedures, it may become necessary to cut and staple various types and thicknesses of tissue, such as, for example, to adjoin hollow organ sections. One exemplary device suitable for cutting and stapling tissue is disclosed in U.S. Pat. No. 5,040,715, to Green et al. the disclosure of which is incorporated herein by reference. Green et al. relates to a surgical stapler for placing lateral lines of staples in tissue and for optionally making an incision therebetween. The device of Green et al. is insertable through an endoscopic tube and utilizes a cartridge assembly to carry the staples. The Green device is thus suitable for use in laparoscopic procedures or open surgery.

In order to properly staple tissue together, it is necessary to use the correct size staple. Thus, during endoscopic procedures, it is often necessary to assess tissue thicknesses in areas of limited accessibility in order to determine the proper staple size to be used. Should too small a staple be used, incomplete staple formation or over compression of the tissue may result, while the use of too large a staple may result in incomplete or loosely stapled tissue. Various devices for measuring tissue thickness are known in the art, such as, for example, U.S. Pat. No. 4,312,363 to Rothfuss et al. While the Rothfuss et al. device may be inserted into a body cavity through a surgical opening, the design and size of the Rothfuss device necessitates a surgical opening that is relatively large, or a body cavity made accessible during extensive surgical procedures.

More suitable devices designed specifically to measure tissue thickness endoscopically are disclosed in commonly assigned EPO Publication No. 0503662. While these devices are capable of measuring tissue thickness endoscopically to aid in determining proper staple sizes, these devices are limited in their functionality to tissue measurement.

SUMMARY

A detachable tissue measuring cartridge is provided for use with a surgical stapling apparatus of the type having an elongate portion, a movable anvil member at a distal end of the elongate portion and an actuating mechanism at a proximal end of the elongate portion. The tissue measuring cartridge includes a housing member which is insertable into the distal end of the elongate portion and a tissue measuring block having a tissue engaging surface movably mounted within the housing member. The measuring block is movable in a vertical direction within the housing member to measure a tissue section captured between the tissue engaging surface and the anvil member. There is also provided means for approximating said tissue engaging surface and the anvil member of the stapling apparatus to capture a tissue section therebetween.

In one embodiment, the approximating means includes at least one wedge member slidably mounted between the housing member and the tissue measuring block. Preferably, actuation of the actuating mechanism of the stapling apparatus drives the wedge member between the housing and the measuring block to thereby move the measuring block upward towards the anvil. The tissue measuring cartridge may further include a biasing means for ensuring consistent degree of compression of the tissue captured between the anvil member and the tissue measuring block. Additionally, gradation lines formed on an outer surface of the tissue measuring block may be provided to give a visual indication of tissue thickness. A cam bar adaptor may be provided to engage the firing mechanism of the surgical stapling apparatus and is operatively connected to the biasing spring such that actuation of the firing mechanism drives the cam bar adaptor and thus the spring and wedge assembly distally to raise the tissue measuring block out of the housing member.

In an alternate embodiment of the tissue measuring cartridge, a tissue measuring block is initially disposed in an upward position within the cartridge housing and a biasing spring positioned between the tissue measuring block and the cartridge housing to bias the block upwardly. Actuation of the anvil member drives the tissue measuring block downwardly within the housing member capture in a tissue section therebetween. Again, gradation lines on the side of the tissue measuring block are provided to give a visual indication of the degree of tissue thickness. Additionally, various block detent and pin mechanisms may be provided on the tissue measuring block and cartridge housing, respectively, to fix or "lock in" the tissue thickness measurement obtained. Finally, the various tissue measuring cartridges may be provided alone or in combination with various actuating mechanisms such as, for example, various surgical stapling, surgical cutting or surgical grasping instrumentation in the form of kits.

A method of measuring tissue thickness is also disclosed and includes the steps of providing a pair operatively associated jaws movable toward and away from each other, at least one of the jaws having a movable tissue engaging block disposed therein, positioning the jaws members about a tissue section, moving one of the jaws toward the other to capture the tissue section therebetween, and driving the block within the associated jaw to compress the tissue section and generate an indication of tissue thickness. In one method the step of driving includes forcing the block at least partially out of the associated jaw toward the opposing jaw. In an alternate method the step of driving includes forcing the block into the associated jaw as the jaws are moved toward one another.

BRIEF DESCRIPTION OF THE DRAWINGS

Various embodiments are described herein with reference to the drawings, wherein:

FIG. 5 is a perspective view, partially shown in section, of a tissue measuring cartridge in accordance with the embodiment of FIG. 1 inserted in a distal end of a surgical actuating apparatus prior to capturing and measuring a tissue section;

FIG. 6 is a view similar to FIG. 5 during actuation of the tissue measuring cartridge in accordance with the embodiment of FIG. 1;

DETAILED DESCRIPTION OF PREFERRED EMBODIMENTS

Because endoscopic procedures are more common than laparoscopic procedures, the present embodiments of the tissue measuring cartridge shall be discussed in terms of endoscopic procedures and apparatus. However, use herein of terms such as "endoscopic", "endoscopically" and "endoscopic portion", among others, should not be construed to limit the tissue measuring apparatus for endoscopic use only. To the contrary, it is believed the tissue measuring cartridge may find use in any procedure where access is limited to a small incision, including but not limited to laparoscopic procedures. Additionally, as used herein, the terms "surgical stapling apparatus", "surgical fastening apparatus", "surgical cutting apparatus", "surgical actuating apparatus" or the like, may be used interchangeably to refer to a surgical apparatus suitable for use with, and actuation of, the various embodiments of the tissue measuring cartridge.

A tissue measuring cartridge is provided which is insertable in a surgical stapling or actuating apparatus in place of a detachable stapling or cutting cartridge. One particularly suitable stapling apparatus for use with the tissue measuring cartridge is disclosed in U.S. Pat. No. 5,040,715 to Green et al., previously incorporated by reference. While the following preferred embodiments are described utilizing a manually actuated surgical stapling apparatus as the actuating mechanism, it can be readily appreciated that various manual or powered surgical apparatus may be used as the actuating apparatus for the tissue measuring cartridge. See, for example, U.S. Pat. No. 5,312,023 to Green et al., the disclosure of which is incorporated herein by reference.

Figure 1:
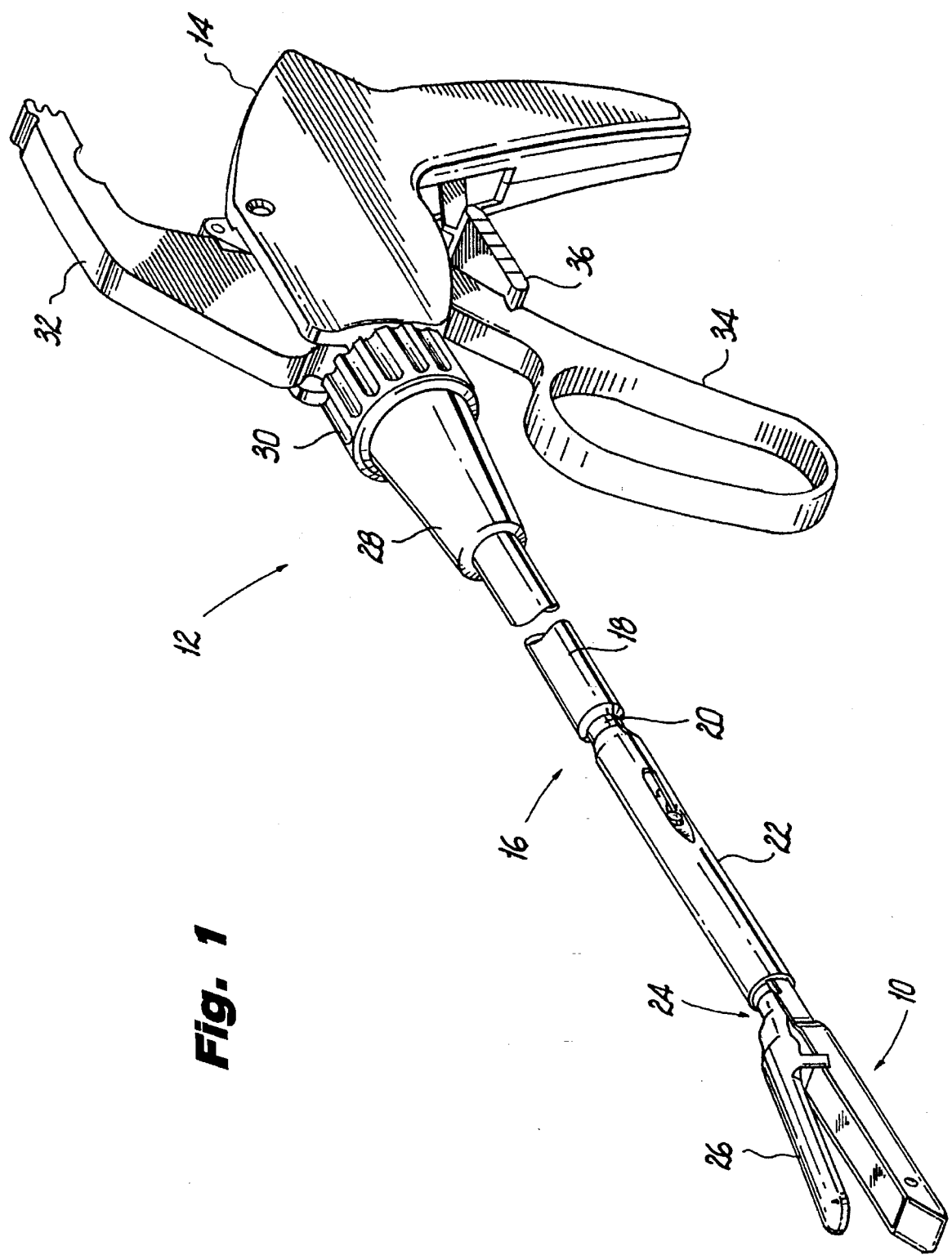
FIG. 1 is a perspective view of the tissue measuring cartridge in accordance with a preferred embodiment inserted in a surgical actuating apparatus.

Referring now to FIG. 1, there is shown a tissue measuring cartridge 10 which is designed to be inserted in a surgical stapling apparatus in place of the staple holding cartridge. A particularly suitable surgical stapling instrument, for use with the tissue measuring cartridge, is disclosed in U.S. Pat. No. 5,318,221 to Green et al. and entitled APPARATUS AND METHOD FOR PLACING STAPLES IN LAPAROSCOPIC OR ENDOSCOPIC PROCEDURES, the disclosure of which is incorporated by reference herein. When tissue measuring cartridge 10 is inserted in a surgical stapling apparatus, the actuation mechanisms of the stapling apparatus actuates the tissue measuring cartridge 10 to hold a tissue section to be measured against tissue measuring cartridge 10 and to actuate the various components thereof. In general, actuating apparatus 12 includes a frame or handle portion 14 having an endoscopic portion 16 extending distally therefrom. Endoscopic portion 16 includes a cover tube 18 which is fixed relative to frame 14. Endoscopic portion 16 further includes an extension tube 20 having a collar tube 22 at the distal end thereof. Extension tube 20 and collar tube 22 are longitudinally slidable relative to frame portion 14 and cover tube 18. Extension tube 20 is slidable within cover tube 18. As more fully described hereinbelow, tissue measuring cartridge 10 is longitudinally insertable within a distal end portion 24 of the endoscopic portion 16.

A movable anvil member 26 is provided at the distal end portion 24 of surgical actuating apparatus 12. Anvil member 26 is movable between an open position spaced apart from tissue measuring cartridge 10 to a closed position adjacent tissue measuring cartridge 10 for capturing a tissue section therebetween. Additionally, there is provided a rotation knob 28 having a knurled surface 30 affixed to cover tube 18. Rotation knob 28 enables the user to rotate the entire endoscopic portion 16, including anvil member 26 and tissue measuring cartridge 10, relative to the frame 14. In this manner, the endoscopic portion may be rotated to position anvil member 26 and tissue measuring cartridge 10 about a particular tissue section when endoscopic section 16 is inserted through a endoscopic tube or small laparoscopic opening.

A clamp handle 32 is pivotally mounted on frame member 14 and is provided to open and close anvil member 26 with respect to tissue measuring cartridge 10 as more fully described hereinbelow. Surgical actuating apparatus 12 further includes a firing handle 34 which is utilized to actuate the various components of the tissue measuring cartridge 10 through a longitudinally movable actuating mechanism disposed within endoscopic portion 16. Additionally, there is provided a manual safety 36 pivotably mounted to frame member 14 for blocking firing handle 34 until such time as it is desired to activate the tissue measuring cartridge 10. While surgical actuating apparatus 12 is described utilizing a manual safety 36, it will be appreciated that various other types and styles of firing or clamp interlock safties may be provided to prevent closure of the anvil member or actuation of the firing handle 34, in the absence of a tissue measuring cartridge 10 or in the event of an improperly inserted tissue measuring cartridge 10.

Figure 2:
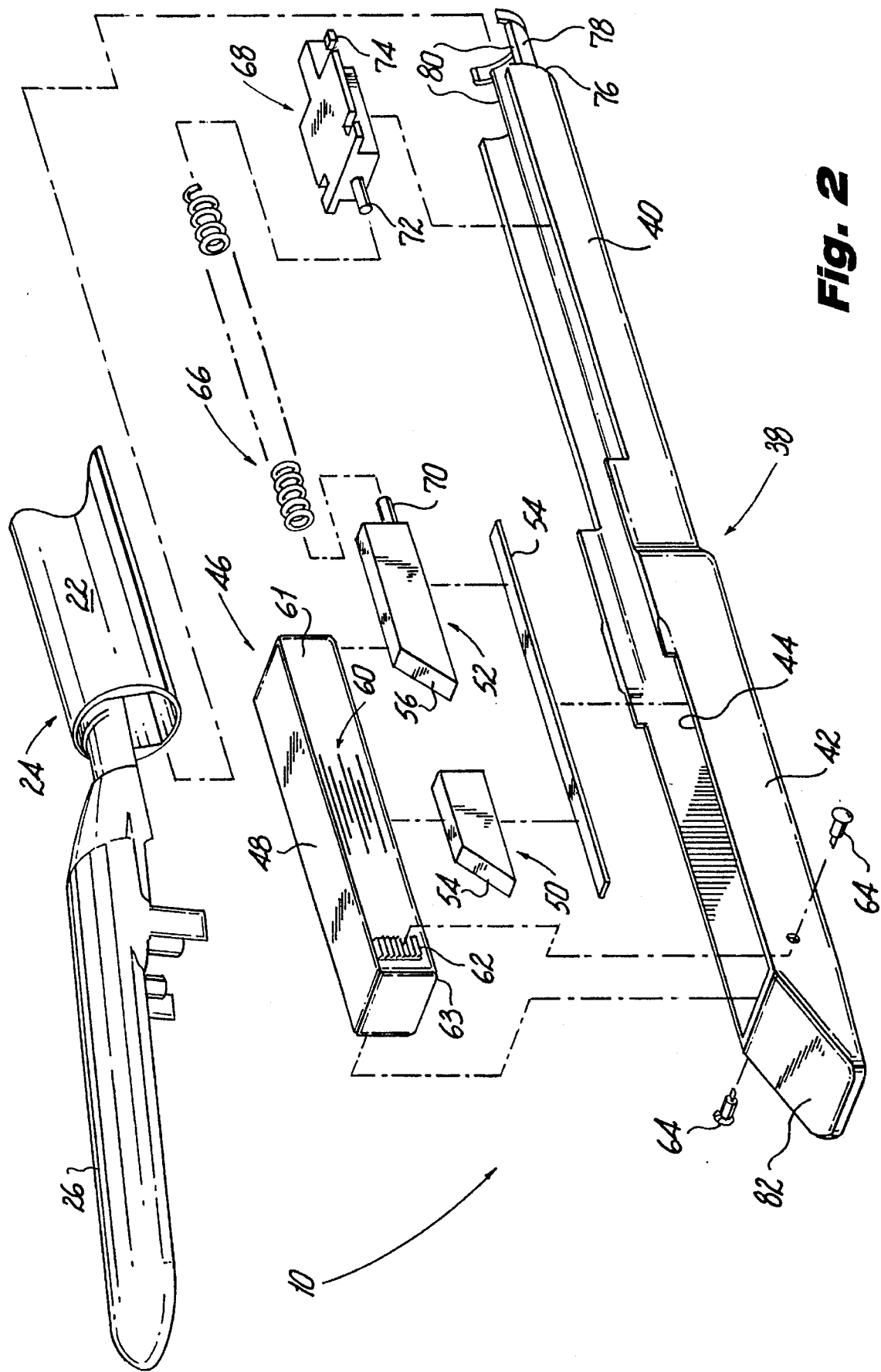
FIG. 2 is an enlarged exploded perspective view of the tissue measuring cartridge in accordance with the embodiment of FIG. 1 and showing a distal end of the surgical actuating apparatus.

Referring now to FIG. 2, there is shown an exploded view of a preferred embodiment of tissue measuring cartridge 10. As noted hereinabove, tissue measuring cartridge 10 is longitudinally insertable in the distal end portion 24 of surgical actuating apparatus 12. Tissue measuring cartridge 10 includes a U-shaped housing member 38 having a proximal housing portion 40 and a distal housing portion 42. Proximal housing portion 40 is longitudinally insertable into distal end portion 24 of actuating apparatus 12. In order to mount tissue measuring cartridge 10 within a distal end portion 24 of surgical actuating apparatus 12, a proximalmost portion 76 of housing member 38 is provided with a mounting portion 78 having mounting portion notches 80 which serve to engage corresponding mounting means on surgical actuating apparatus 12. A housing channel 44 extends longitudinally substantially the length of housing member 38. Housing member 38 may be provided with an angled distal face 82 which serve to atraumatically guide a tissue section between tissue measuring cartridge 10 and anvil member 26.

A movable tissue measuring block 46 is provided within housing channel 44 at distal housing portion 42 and includes a tissue engaging upper surface 48 which cooperates with anvil member 26 to capture and measure a tissue section therebetween. Tissue measuring block 46 is movable in a vertical direction relative to housing member 38.

While various mechanisms may be provided to raise and lower tissue measuring block 46 within housing channel 44, it is particularly desirable to provide a pair of wedge members such as forward wedge member 50 and rear wedge member 52, each having an angled face 56 and 58, respectively thereon, to drive tissue measuring block 46 vertically with respect to housing member 38. Preferably, forward wedge member 50 and rear wedge member 52 are mounted on a longitudinally slidable wedge sled 54 which serves to maintain wedge members 50, 52 in spaced apart relation. Angled faces 56, 58 cooperate with corresponding angled faces 55 and 57 (FIG. 5) on an inner surface of tissue measuring block 46 to drive tissue measuring block 46 vertically as the wedge members 50, 52 are driven longitudinally. In the embodiment of FIGS. 1–7, wedge members 50 and 52, along with wedge sled 54 are approximating means for moving tissue engaging surface 48 toward anvil member 26.

A plurality of gradation lines 60 may be provided on side surfaces 61 of tissue measuring block 46 to give a visual indication of the compressed tissue thickness. By reading the tissue thickness from gradation lines 60, the appropriate size staple, and thus the proper staple cartridge, may be selected. Additionally, detents 62 are provided in side surfaces 61 and are engagable with retaining pins 64 movably mounted through housing 38. Detents 62 and retaining pins 64 cooperate to "lock in" a measurement obtained as tissue measuring block 46 is raised out of channel 44.

As noted hereinabove, firing handle 34 is provided to actuate the tissue measuring cartridge. Drawing firing handle 34 proximally drives a longitudinally movable actuating mechanism which is provided to move wedge members 50, 52 and wedge sled 54 longitudinally to within housing channel 54 to cam or raise tissue measuring block 46. While the longitudinally movable actuating mechanism of actuating apparatus 12 may be connected directly to wedge sled 54 or rear wedge member 52, and thereby provide a tactile feel of the amount of tissue compression between tissue measuring surface 48 and anvil member 26, it is preferable to connect the actuating mechanism of surgical actuating apparatus 12 to rear wedge member 52 by means of a spring 66. Spring 66 is provided to ensure a consistent degree of force exerted against rear wedge member 52 and thus a consistent degree of tissue compression between tissue measuring block 46 and anvil member 26. Preferably spring member 66 is positioned between rear wedge member 52 and a cam bar adapter 68 which serves to directly engage the actuating mechanism of surgical actuating apparatus 12. Spring 66 is preferably connected to a pin 70 on rear wedge member 52 and a pin 72 on cam bar adapter 68 in friction fit fashion. It will be noted that cam bar adapter 68 is disposed within proximal portion 40 of housing member 38 and is longitudinally slidable within housing channel 44. Cam bar adapter 68 may preferably be provided with a pair of cam bar adapter tabs 74 which serve to directly engage a distal portion of the actuating mechanism of surgical actuating apparatus 12.

Figure 3:
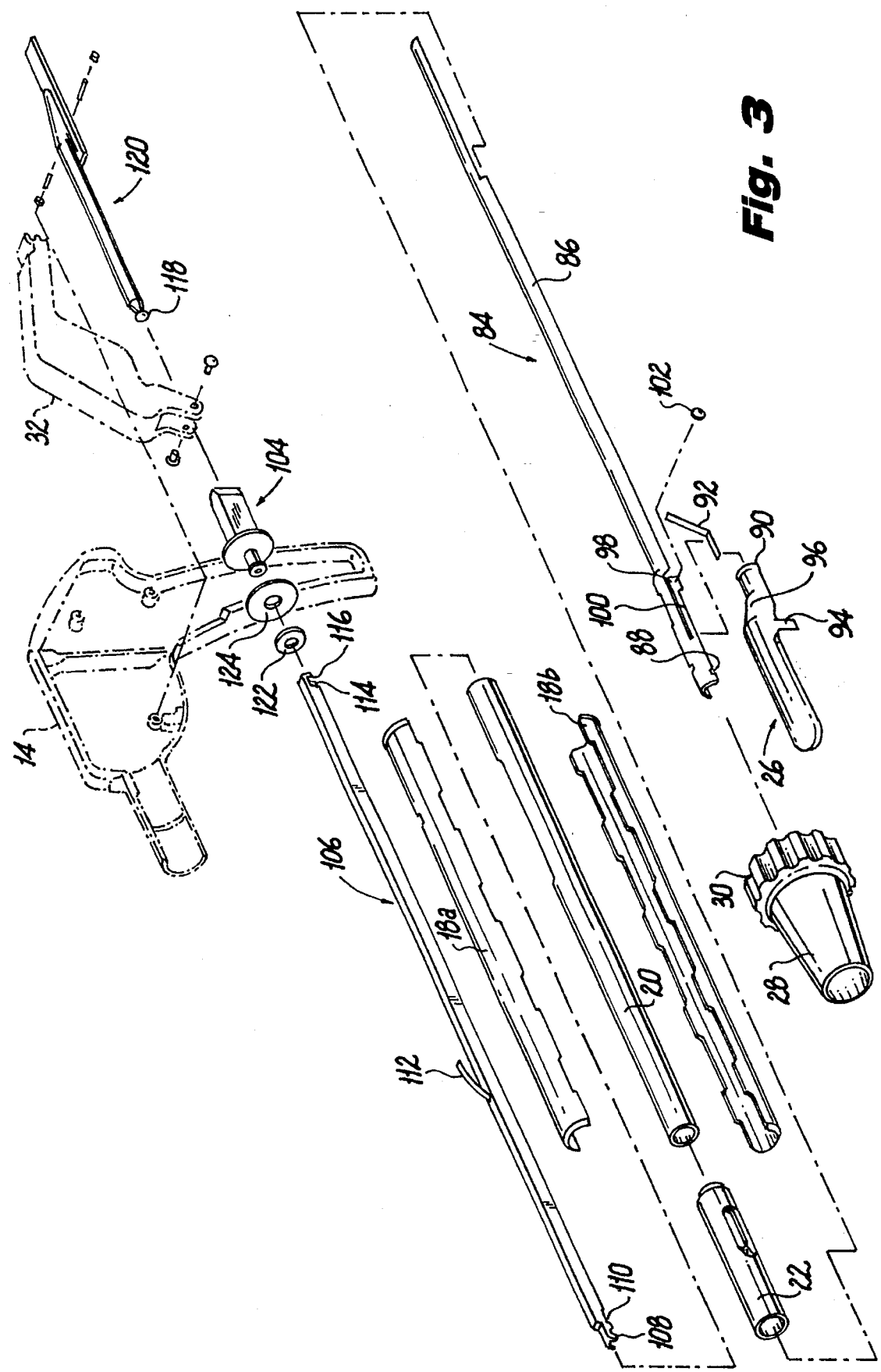
FIG. 3 is an exploded perspective view of a portion of a surgical actuating apparatus suitable for use with the tissue measuring cartridge of the present invention.
Figure 4:
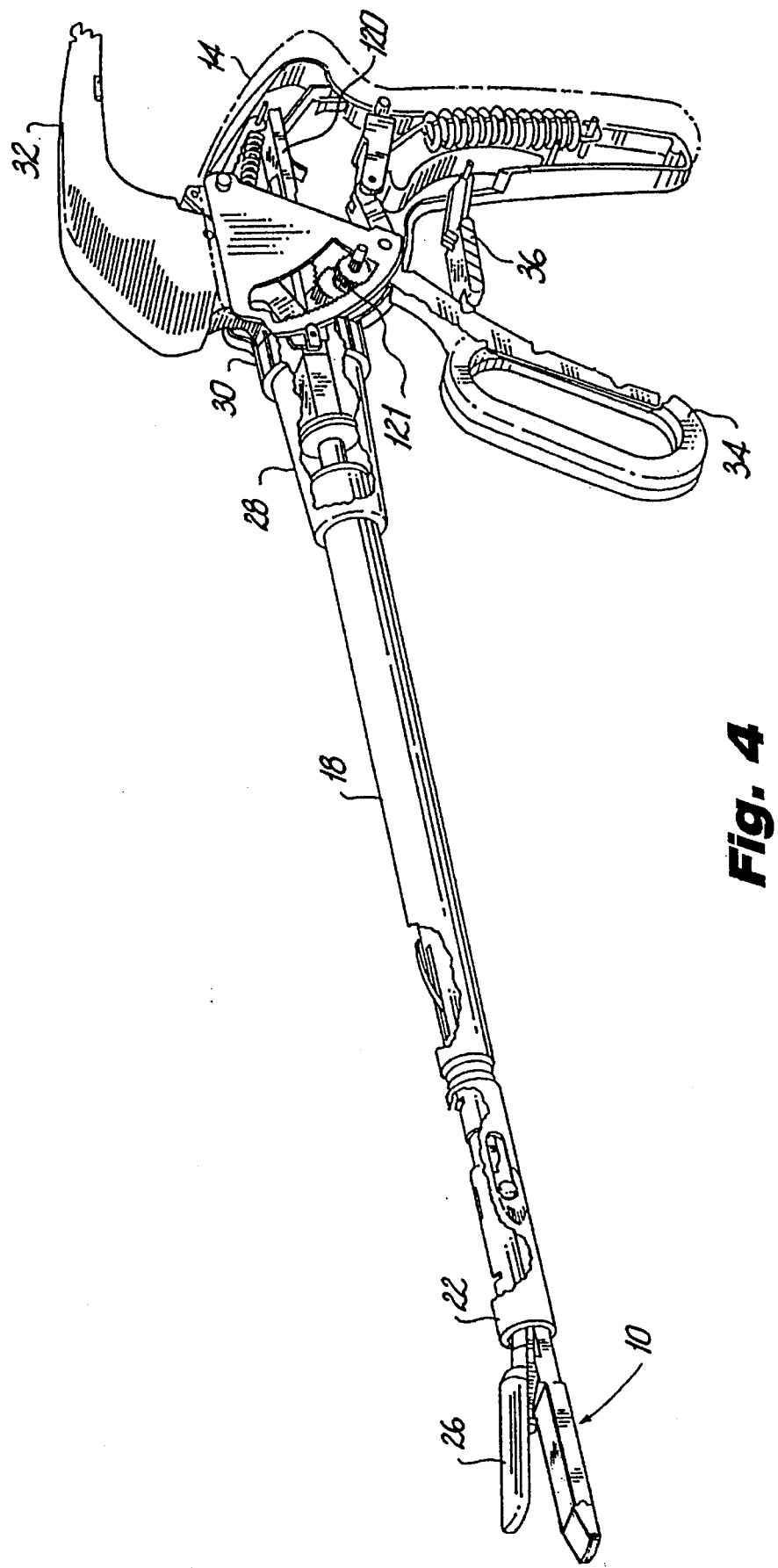
FIG. 4 is a perspective view, partially shown in break away, of the surgical actuating apparatus of FIG. 1.

Referring now to FIGS. 2, 3 and 4, and initially to FIG. 3, surgical actuating apparatus 12 includes a support 84 which is fixed at its proximal end to frame 14 and is provided to mount and maintain tissue measuring cartridge 10 and anvil member 26 in longitudinally fixed relationship relative to surgical actuating apparatus 12. Support 84 includes a central portion 86 which is positioned within cover tube halves 18a and 18b. A pair of transverse slots 88 are provided at a distal end of support 84 and serve to engage corresponding anvil projections 90 on anvil member 26 to mount anvil member 26 thereon. Leaf spring member 92 is provided between anvil member 26 and support 84 and serves to bias anvil member 26 into an open position. Anvil member 26 may additionally include a pair of downwardly extending tissue stops 94 which aid in preventing over-insertion of a tissue section between anvil member 26 and tissue measuring cartridge 10.

Anvil member 26 is movable between an open position spaced apart from tissue measuring cartridge 10 to a closed position adjacent tissue measuring cartridge 10. To move anvil 26 between the open and closed positions a camming surface 96 on anvil 26 is engaged by collar tube 22 as collar tube 22 is driven longitudinally in order to cam anvil member 26 from the open position to the closed position. A clamp tube 104 is provided to connect clamp handle 32 to extension tube 20 as more fully described in U.S. Pat. No. 5,318,221. Thus, by opening or closing clamp handle 32, extension tube 20 and thus collar tube 22 is moved longitudinally along the endoscopic portion 16 to cam open and closed anvil member 26.

As noted herein above, tissue measuring cartridge 10 is removably mountable to surgical actuating apparatus 12. To hold tissue measuring cartridge 10 in position on surgical actuating apparatus 12, support member 84 includes a pair of ramped forward ends 98 which engage notches 80 on mounting portion 78 of tissue measuring cartridge 10. Ramped forward ends 98 are affixed to support 84 by means of a pair of flexible attaching ends 100. To release tissue measuring cartridge 10 from surgical actuating apparatus 12, a release button 102 is affixed to one of ramped forward ends 98 and, when depressed radially inwardly, serves to disengage ramped end 98 from notches 80 to thereby release tissue measuring cartridge 10 from surgical actuating apparatus 12.

As noted above, firing handle 34 is provided to actuate tissue measuring cartridge 10. Referring to FIGS. 2 and 3, the longitudinally movable actuating mechanism of actuating apparatus 12 generally includes a channel member 106 having a pair of forks 108 at a distal end thereof which engage cam bar adapter tab 74 to connect channel 106 to cam bar adapter 68. Additionally, abutting structure 110 is provided to urge cam bar adapter 68 distally within housing member 38. A biasing spring 112 is affixed to channel member 106 to urge channel member 106, and thus abutting structure 110, downwardly within endoscopic portion 16. Should tissue measuring cartridge 10 be improperly mounted within endoscopic portion 16, or, if cam bar adapter 68 is not at a proximalmost position, forks 108 will not lift up to engage cam bar adapter 68 and thus downwardly biased abutting structure 110 will "jam" within endoscopic portion 16 to "lock out" channel member 106 from longitudinal movement.

Referring now to FIG. 4, rod rack 120 is connected to firing handle 34 by means of a gear mechanism 121, the operation of which is more fully disclosed in U.S. patent application Ser. No. 07/943,403. A proximal end of channel 106 is provided with a pair of fingers 114 having slots 116 which engage a push plug 118 on a rod rack 120 to drive channel member 106 longitudinally within endoscopic portion 16. Drawing firing handle 34 proximally drives gear mechanism 121 which in turn drives rod rack 120 distally. As rod rack moves distally, channel member 106 (FIG. 3) moves distally thereby driving cam bar adapter 68 distally within proximal portion 40 of housing member 38 (FIG. 2). Inner and outer gas seals 122 and 124, respectively, are provided to prevent the escape of gas through endoscopic portion 16 should the surgical apparatus be used in an insufflated body cavity.

Referring now to FIGS. 1 and 5–7, the operation of tissue measuring cartridge 10 in the surgical actuating apparatus 12 will be described. Initially, a small laparoscopic incision or an endoscopic tube are inserted within a body and the body insufflated to provide a working space for a cavity. The appropriate tissue section, such as, for example, a tubular tissue section is located. Clamp handle 32 is opened to raise anvil member 26 relative to a longitudinal axis of endoscopic portion 16 and tissue measuring cartridge 10 is inserted into endoscopic portion 16 in the manner described hereinabove. Ramped forward ends 98 on support member 84 engage notches 80 in mounting portion 78 to securely and positively mount tissue measuring cartridge 10 within distal end portion 24 of surgical actuating apparatus 12. As tissue measuring cartridge 10 is inserted into surgical actuating apparatus 12, forks 108 of channel 106 ride up and over and engage tab portion 74 of cam bar adapter 68. In this manner, tissue measuring cartridge 10 is properly mounted within surgical actuating apparatus 12 and is in a condition ready to be fired. Cam bar adapter and thus wedge members 50, 52 and wedge slide 54 are in a proximalmost position and tissue measuring block 46 is fully seated within housing member 38. Clamp member 32 is closed to drive collar tube 22 distally thereby camming anvil member 26 to a closed position adjacent tissue measuring cartridge 10 and the endoscopic portion 16 of surgical actuating apparatus 12 is inserted into the body. Once inserted, handle member 32 is opened to allow collar tube 22 to move proximally enabling anvil member 26 to open against the bias of spring 92.

As shown in FIG. 5, when in an open position, anvil member 26 and tissue measuring cartridge 10 are positioned about a tissue section to be measured. Downwardly projecting portions 94 of anvil member 26 serve as tissue stops and prevent over-insertion of a tissue section between anvil member 26 and tissue measuring cartridge 10. Referring now to FIG. 6, closing clamp handle 32 drives collar tube 22 distally to cam anvil member closed about the tissue section. Surgical actuating apparatus 12 is now in a condition ready to fire to generate a tissue measurement. Manual safety 36 is pivoted downwardly away from firing handle 34 and firing handle 34 is pulled proximally to drive channel member 106 distally. As channel member 106 is driven distally it drives cam bar adapter 68 and thus spring 66 distally. Distal movement of spring 66 drives rear wedge member 52 distally, and thus by means of wedge sled 54 drives forward wedge member 50 distally. As noted hereinabove, angled faces 56, 58 of wedge members 50, 52, respectively, engage corresponding angled faces 55 and 57 of tissue measuring block 46 to thereby drive tissue measuring block 46 upwardly and out of housing member 38. As firing handle 34 is closed and tissue measuring block 46 is raised out of housing member 38, spring 66 compresses to a predetermined pressure to ensure consistent compression and thus a consistent measurement of the thickness of the captured tissue section.

Gradations 60 on tissue measuring block 46 are lined up with a top edge of distal housing portion 42 to allow a tissue thickness measurement to be read. This may be done either endoscopically during the operation or detents 62 formed on outside edges of tissue measuring block 46 may be engaged by retaining pins 64, as more specifically shown in FIG. 7 to "lock in" the tissue measurement generated. It is noted that pins 64 ride over angled surfaces 61 of detents 62 to allow tissue measuring block 46 to be raised within channel 44, level surfaces 63 on detents 62 prevent pins 64 from allowing tissue measuring block 46 from slipping down within channel 44 and thereby lose the measurement previously obtained. Drawing pins 64 away from detents 62 allows tissue measuring block 46 to be reset for subsequent use and measurements. Thus, upon opening anvil 26 away from tissue measuring block 10, tissue measuring block 46 remains in a raised or upright position at which point the surgical actuating apparatus 12 may be removed and the degree of tissue thickness read off the gradations 60.

It will be noted that as firing handle 34 is released, channel 106 moves proximally within an endoscopic portion 16. Thus, channel member 106 draws cam bar adapter 68 proximally within proximal housing portion 40. Channel member 106 may disengage from cam bar adapter 68 upon proximal movement thereof or, more preferably, spring 66 disengages from its friction fit connection with either pin 70 or 72 to thereby disengage cam bar adapter 68 from rear wedge member 52.

Figure 8:
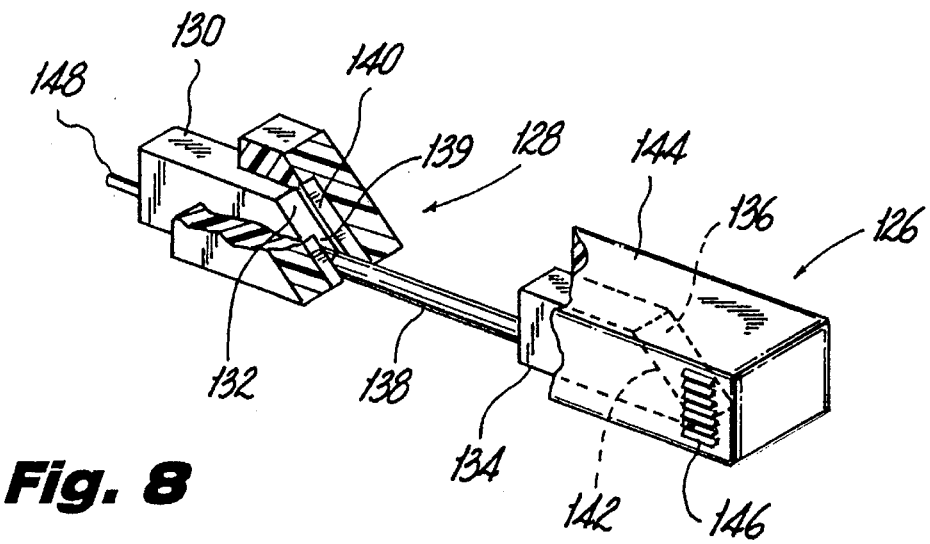
FIG. 8 is a perspective view, partially shown in section, of an alternate embodiment of the tissue measuring block and wedge assembly.
Figure 7:
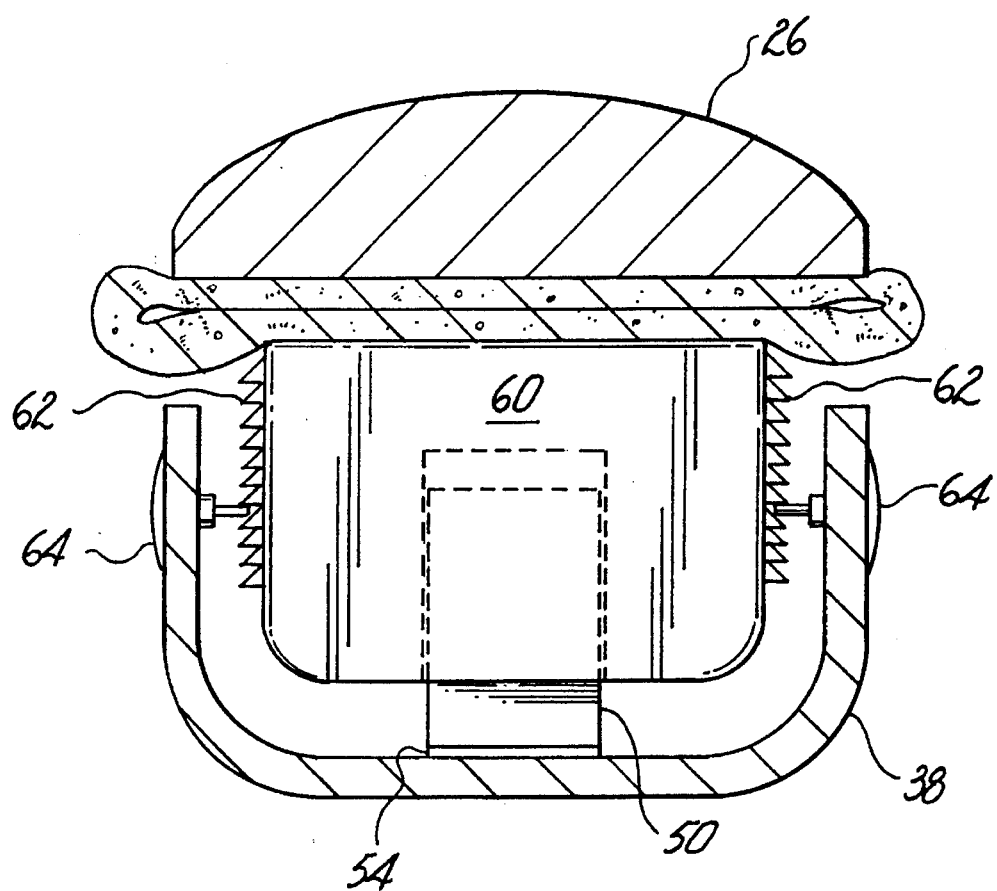
FIG. 7 is an cross-sectional view taken along the lines 7—7 of FIG. 6, showing the tissue measuring cartridge in accordance with the embodiment of FIG. 2 and an anvil member closed about the tissue section.

Referring now to FIG. 8, there is disclosed an alternate tissue measuring block 126 and wedge assembly 128 for use with tissue measuring cartridge 10. Wedge assembly 128 generally includes a rear wedge member 130 having an angled driving face 132 and a forward wedge member 134 having an angled driving face 136. In order to provide a rigid connection between rear wedge member 130 and forward wedge member 134, there is provided a wedge bar 138 connecting rear wedge member 130 to forward wedge member 134. Preferably wedge bar 138 is cylindrical in cross section and solid. Wedge bar 138 provides a more rigid connection between wedge members 130 and 134 to prevent any inadvertent flexing, as may be the case with relatively flat wedge sled 54, when taking tissue measurements of relatively stiff or dense tissue sections. Angled driving faces 132 and 136 engage corresponding angled drive faces 140 and 142 on tissue measuring block 126 to drive tissue measuring block 126 upwardly and out of housing channel 44 as wedge assembly 128 is driven distally. Tissue measuring block 126 further includes a tissue engaging surface 144 similar to tissue engaging surface 48 described hereinabove and a plurality of detent members 146 which cooperate with retaining pins 64 to maintain tissue measuring block 126 in an upward position. Rear wedge member 130 may also be provided with a rear wedge spring pin 148 which functions substantially similar to spring pin 70 described hereinabove. In the embodiment of FIG. 8, wedge assembly 128, including wedge bar 138, forms approximating means for moving tissue engaging surface 144 toward anvil member 26.

In order to provide clearance for wedge bar 138, tissue measuring block 126 is provided with a longitudinal channel 139 extending between angled face 140 and a distal end of forward wedge member 134. Additionally, tissue measuring block 126 may be provided with gradation lines (not shown) on an outer surface thereof which functions substantially similar to gradation lines 60 on tissue measuring block 46. In use, the operation of alternate tissue measuring block 126 and wedge assembly 128 is identical to that disclosed with respect to tissue measuring block 46 and wedge members 50, 52 and wedge sled 54 described hereinabove.

Figure 9:
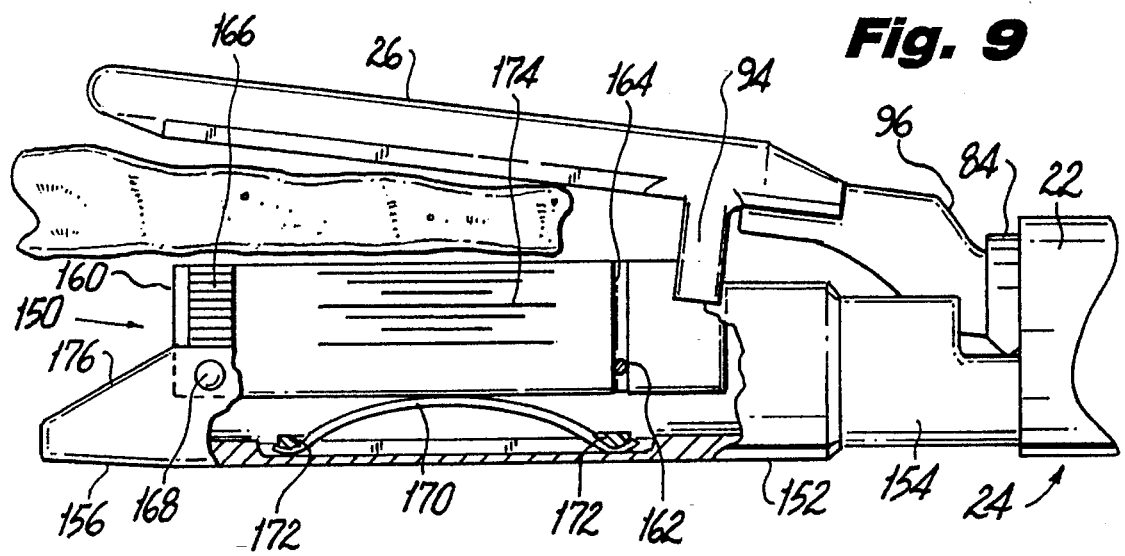
FIG. 9 is a side elevation view, partially shown in section, of an alternate embodiment of the tissue measuring cartridge inserted in a distal end of a surgical actuating apparatus and prior to closure about a tissue section.
Figure 10:
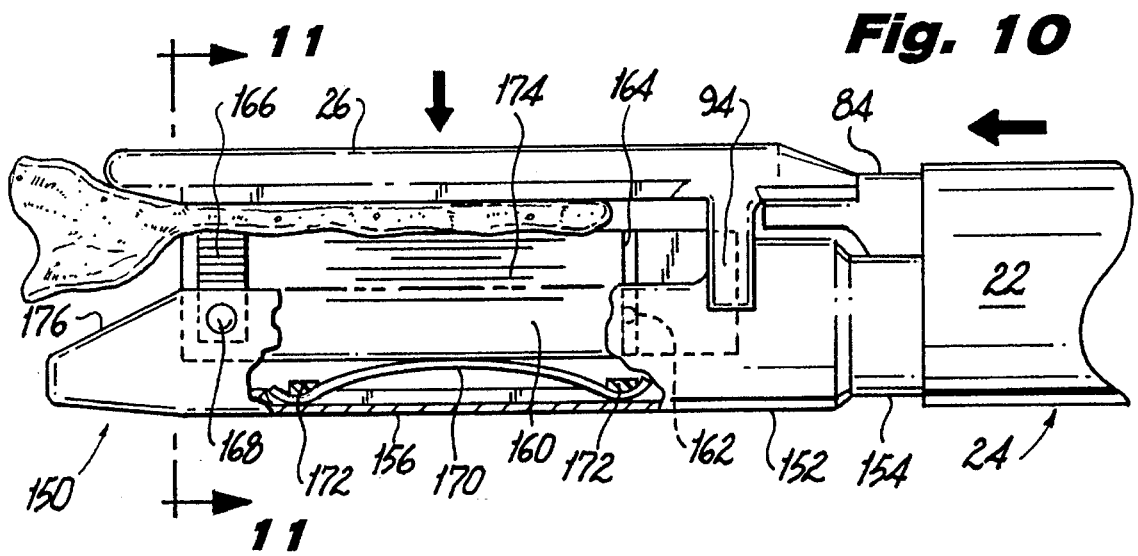
FIG. 10 is a view similar to FIG. 9 during closure about, and measurement of, a tissue section.
Figure 11:
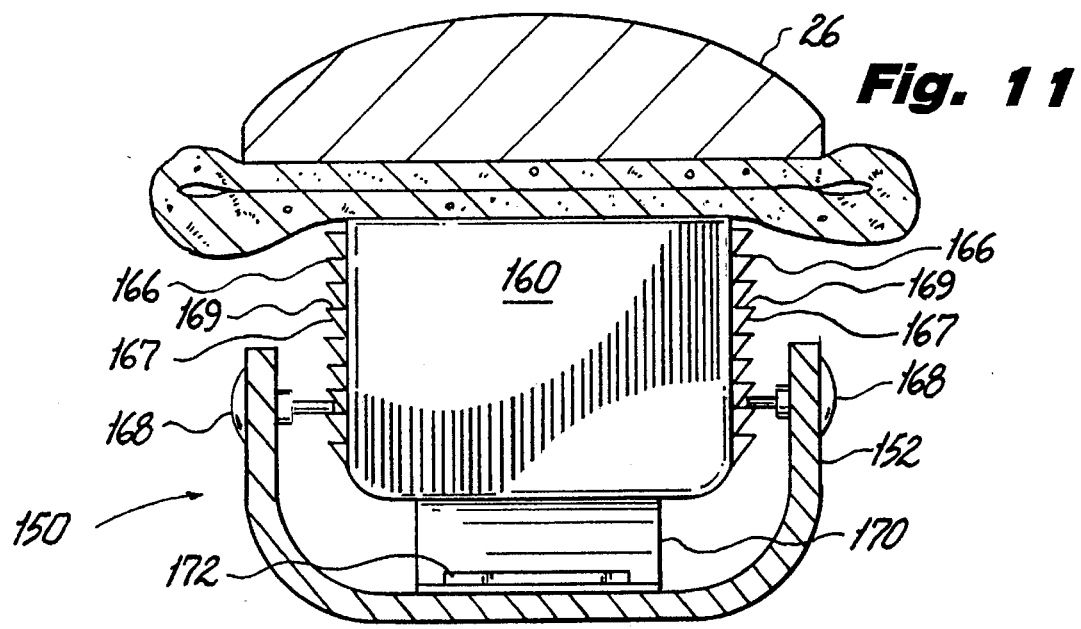
FIG. 11 is cross sectional view of the embodiment of FIG. 10 taken along line 11—11 of FIG. 10.

Referring now to FIGS. 9–11, there is disclosed an alternate embodiment of the tissue measuring cartridge. Tissue measuring cartridge 150 is demountably attachable to distal end portion 24 of surgical actuating apparatus 12 and is operable solely by the actuation of the clamping mechanism, i.e. clamp handle 32, anvil 26 and associated components thereof, to actuate the tissue measuring cartridge and achieve an indication of tissue thickness, thus eliminating the need for a firing mechanism.

Tissue measuring cartridge 150 generally includes a U-shaped housing 152 having a proximal housing portion 154 and a distal housing portion 166. A housing channel 158 extends longitudinally throughout substantially the length of U-shaped housing 152. A tissue measuring block 160 is provided and it is vertically movable within housing channel 158. It will be noted that tissue measuring block 160 is initially disposed in an upward or raised out of housing 152 condition. In order to prevent any distal to proximal tilting of tissue measuring block 160, a guide pin 162 is provided on an inner surface of proximal housing portion 154 and cooperates with a block pin recess 164 in tissue measuring block 160. Guide pin 162 rides vertically within block pin recess 164 to guide tissue measuring block 160 in its vertical travel within U-shaped housing member 152. Tissue measuring block 160 is also provided with a plurality of block detents 166 provided at a distal end thereof which cooperate with a pair of transversely movable detent pins 168 mounted in distal housing portion 156. Block detents 166 have an angled face 167 and a flat face 169, as shown more clearly in FIG. 11, which allow pins 168 to ride over angled faces 167 as tissue measuring block 160 is forced downwardly within housing channel 158. Flat surfaces 169 prevent tissue measuring block 160 from rising up out of housing channel 158 until detent pins 168 are released therefrom.

In order to maintain tissue measuring block 160 in an upward position within housing channel 158 and to provide a predetermined degree of compression of tissue captured between tissue measuring block 160 and anvil member 126, there is provided a leaf spring 170 flexibly mounted in a base of U-shaped housing 152. A pair of leaf spring retainers 172 are provided at each end of lead spring 170 to hold leaf spring 170 in place within channel 158. Tissue measuring block 160 may include a plurality of gradation lines 174 for generating a visual indication of the tissue thickness and thus the size of the staples to be selected. Additionally, U-shaped housing may have an angled face 176 which serves to guide a tissue section atraumatically between tissue measuring cartridge 150 and anvil member 26.

Proximal housing portion 154 is substantially identical to proximal housing portion 40 as described with respect to tissue measuring cartridge 10 above and includes a mounting portion 78 at a proximal end 76 having mounting portion notches 80 which engage ramped forward ends 98 on support 84 to thereby detachably mount tissue measuring cartridge 150 on surgical actuating apparatus 12.

Referring now to FIGS. 1 and 9–11, the operation of tissue measuring cartridge 150 will be described. Tissue measuring cartridge 150 is mounted on surgical actuating apparatus in a manner identical to that described with respect to tissue measuring cartridge 10 hereinabove and surgical actuating apparatus is inserted endoscopically to position open anvil member 26 and tissue measuring cartridge 150 about a tissue section to be measured. As noted hereinabove, tissue measuring cartridge 150 is actuable solely due to the clamping action of the anvil member about the tissue section. Thus, as clamp handle 32 is closed to drive collar tube 22 distally, collar tube 22 engages camming surface 96 and anvil member 26 to cam anvil member 26 to a closed position towards tissue measuring cartridge 150. As anvil member 26 moves toward tissue measuring cartridge 150, and compresses a tissue section therebetween, the compressed tissue section engages tissue measuring surface 161 thereby driving tissue measuring block 160 downwardly into housing channel 158. In the embodiment of FIGS. 9–11, clamp handle 32, collar tube 22 and camming surface 96 are means for moving anvil member 26 between an open and closed position.

As noted hereinabove, pin 162 rides in recess 164 to guide tissue measuring block 160 downwardly into housing channel 158. The degree of tissue thickness may be read off gradation lines 174 which line up with an edge of U-shaped housing member 152. Pins 168 cooperate with detents 166 to secure or "lock in" the tissue measurement obtained. As noted hereinabove, as block 160 is driven downwardly within housing channel 158, spring 170 provides an upward bias to ensure a consistent degree of compression of the tissue section to be measured.

As with tissue measuring cartridge 10 described hereinabove, a reading of the degree of tissue thickness may be made endoscopically or, upon release of the tissue section from anvil member 26 surgical actuating apparatus 12 may be withdrawn from the body and the degree of tissue thickness read off of gradation lines 174. In this manner, a generation of the measurement of tissue thickness may be had utilizing only the clamping or moving jaw action of the surgical actuating apparatus 12.

It will be understood that various modifications may be made to the embodiments disclosed herein. For example, various other methods of moving the measuring block, such as, for example, cams, rack and pinions, inflatable methods, etc. may be employed. Additionally other indicators, such as, color coding, graphic or other representations positioned on the tissue measuring cartridge or on the actuating apparatus may be used to indicate the tissue thickness. Further various jaw structure such as clamping, grasping, cutting or other movable jaw structures may be utilized in connection with the various tissue measuring cartridge embodiments as actuating the apparatus to obtain tissue measurements. The actuation of a tissue measuring cartridge either through the clamping action of a jaw structure or the actuation of a longitudinally movable actuating member may additionally be incorporated in a non-detachable version of a tissue measuring apparatus. Therefore, the above description should not be construed as limiting, but merely as exemplifications of preferred embodiments. Those skilled in the art will envision other modifications within the scope and spirit of the claims appended hereto.

What is claimed is:

1. A tissue measuring cartridge for use with a surgical stapling device having an elongate portion, an anvil at a distal end thereof and an actuator, said cartridge comprising:

a) a housing member having a mounting portion which releasably attaches adjacent the distal end of the elongate portion;

b) a measuring block having a tissue engaging surface and being mounted within the housing member for movement from a first position to a second position, the second position corresponding to a thickness of tissue captured between the anvil and the tissue engaging surface of the measuring block; and c) means for approximating said tissue engaging surface and the anvil to capture and measure tissue.

2. The tissue measuring cartridge according to claim 1, further comprising an indicator to indicate the thickness of the captured tissue.

3. The tissue measuring cartridge according to claim 1, wherein the approximating means is operatively associated with the actuator of the stapling device such that actuation of the actuator causes the approximating means to move the measuring block towards the anvil to thereby capture tissue therebetween.

4. The tissue measuring cartridge according to claim 3, wherein the approximating means includes a wedge member mounted within the housing member, such that actuation of the actuator drives the wedge member into engagement with the measuring block to thereby move the measuring block towards the anvil.

5. The tissue measuring cartridge according to claim 4, wherein said approximating means further includes a biasing system to exert a predetermined force on the tissue captured between the tissue measuring block and the anvil.

6. The tissue measuring cartridge according to claim 5, wherein the biasing system includes a spring disposed between the wedge member and the actuator.

7. The tissue measuring cartridge according to claim 6, further comprising a cam bar adaptor disposed between the spring and the actuator, the cam bar adaptor being engagable with the actuator to compress the spring in response to actuation of the actuator.

8. A surgical apparatus for measuring body tissue comprising:
  a) a frame;
  b) an endoscopic portion defining a longitudinal axis and extending distally from the frame;
  c) an anvil member having a tissue engaging surface and a proximal end mounted to a distal end of the endoscopic portion;
  d) a tissue measuring cartridge mounted to the distal end of the endoscopic portion, the cartridge including:
    i) a housing member; and
    ii) a measuring block having a tissue engaging surface and movably mounted within the housing member; and
  e) an actuator operatively associated with the frame and with the measuring block, wherein actuation of the actuator moves the measuring block towards the anvil member to capture a tissue section between the tissue engaging surface of the measuring block and the tissue engaging surface of the anvil member.

9. The surgical apparatus according to claim 8, further comprising an indicator to indicate the thickness of the captured tissue.

10. The surgical apparatus according to claim 8, wherein the tissue measuring cartridge further includes a slidable wedge member disposed between the housing member and the measuring block, the wedge member engagable with the actuator, wherein actuation of the actuator drives the wedge member between the housing member and the measuring block to move the measuring block towards the anvil member.

11. The surgical apparatus according to claim 10, wherein the tissue measuring cartridge further includes a lock mechanism to maintain the measuring block in a raised position out of the housing after actuation of the actuator.

12. The surgical apparatus according to claim 10, wherein the tissue measuring cartridge further includes a biasing mechanism to exert a predetermined force on the captured tissue by the measuring block.

13. The surgical apparatus according to claim 12, wherein the biasing mechanism includes a spring associated with the wedge member and engagable with the actuator to exert a predetermined force on the wedge member in response to actuation of the actuator.

14. The surgical apparatus according to claim 13, wherein said tissue measuring cartridge further includes a cam bar adaptor engagable with a proximal end of the spring and a distal end of the actuating mechanism.

15. The surgical apparatus according to claim 14, wherein the actuator includes a movable lever mounted to the frame and a push rod slidably disposed within the endoscopic portion, a proximal end of the push rod engagable with the lever and a distal end of the push rod engagable with the cam bar adaptor such that the movement of the lever causes a corresponding movement of the cam bar adaptor.

16. The surgical apparatus according to claim 8, wherein the tissue measuring cartridge is detachable from the distal end of the endoscopic portion.

17. A surgical apparatus for measuring body tissue comprising:
  a) a frame;
  b) an endoscopic portion defining a longitudinal axis and extending distally from the frame;
  c) a tissue measuring cartridge having a tissue engaging surface and mounted to a distal end of the endoscopic portion;
  d) an anvil member having a tissue engaging surface thereon and a proximal end mounted to the distal end of the endoscopic portion such that the anvil member is movable between an open position and a closed position wherein the anvil tissue engaging surface is in close cooperative alignment with the tissue engaging surface of the cartridge; and
  e) means for moving the anvil member between the open and the closed position, wherein the tissue measuring cartridge is detachable from the endoscopic portion.

18. The surgical apparatus according to claim 17, wherein the tissue measuring cartridge includes a housing member attached to the distal end of the endoscopic portion and a tissue measuring block movably disposed within the housing member and initially raised partially out of the housing such that when the anvil member and the tissue measuring cartridge are positioned about a tissue section and the anvil member is moved to the closed position about the tissue section, the measuring block is moved downwardly within the housing member.

19. The surgical apparatus according to claim 18, wherein the tissue measuring block includes an indicator to indicate the amount of movement between the measuring block and the housing member.

20. A surgical apparatus for measuring body tissue comprising:
  a) a frame;
  b) an endoscopic portion extending distally from the frame;
  c) a pair of jaw members operatively associated with a distal end of the endoscopic portion, at least one of the jaw members being movable with respect to the other jaw members; and
  d) a measuring member movably mounted on at least one of the jaws such that movement of one jaw towards the other to capture a tissue section therebetween moves the measuring member with respect to the associated jaw to give an indication of the thickness of the captured tissue.

21. A method of measuring tissue thickness comprising the steps of:
  a) providing a pair of operatively associated jaws movable toward and away from each other, at least one of the jaws having a movable tissue engaging block disposed therein;

b) positioning the jaws members about a tissue section;

c) moving one of the jaws toward the other to capture the tissue section therebetween; and d) driving the block within the associated jaw to compress the tissue section and generate an indication of tissue thickness.

22. The method according to claim 21, wherein the step of driving includes forcing the block at least partially out of the associated jaw towards the opposing jaw to compress the tissue section therebetween and generate an indication of tissue thickness.

23. The method according to claim 21, wherein the step of driving includes forcing the block into the associated jaw as the jaws are moved toward one another to capture the tissue section therebetween and generate an indication of tissue thickness.

* * * * *